(12) United States Patent
Dutscher et al.

(10) Patent No.: US 10,154,665 B2
(45) Date of Patent: Dec. 18, 2018

(54) TEST TUBE WITH IDENTIFICATION DEVICE AND CORRESPONDING PRODUCTION METHOD

(71) Applicant: BIOSIGMA SRL, Cona (IT)

(72) Inventors: Dominique Charles Joseph Dutscher, Haguenau (FR); Martino Marcolin, Piove di Sacco (IT); Francesco Tamiazzo, Piove di Sacco (IT); Valter Veronese, Piove di Sacco (IT)

(73) Assignee: BIOSIGMA SRL, Cona (IT)

( * ) Notice: Subject to any disclaimer, the term of this patent is extended or adjusted under 35 U.S.C. 154(b) by 911 days.

(21) Appl. No.: 14/403,034

(22) PCT Filed: May 23, 2013

(86) PCT No.: PCT/IB2013/001009
§ 371 (c)(1),
(2) Date: Nov. 21, 2014

(87) PCT Pub. No.: WO2013/175293
PCT Pub. Date: Nov. 28, 2013

(65) Prior Publication Data
US 2015/0157011 A1 Jun. 11, 2015

(30) Foreign Application Priority Data

May 23, 2012 (IT) .............................. UD2012A0094

(51) Int. Cl.
*B01L 3/00* (2006.01)
*A01N 1/02* (2006.01)
(Continued)

(52) U.S. Cl.
CPC ............ *A01N 1/0268* (2013.01); *B01L 3/502* (2013.01); *B01L 3/5453* (2013.01); *C12M 45/22* (2013.01);
(Continued)

(58) Field of Classification Search
CPC .......... B01L 3/50; B01L 3/502; B01L 3/5021; B01L 3/54; B01L 3/545; B01L 3/5453;
(Continued)

(56) References Cited

U.S. PATENT DOCUMENTS 6,372,293 B1 * 4/2002 Mathus ................ B01L 3/5453
156/239
6,652,812 B1 11/2003 Vartiainen et al.
(Continued)

FOREIGN PATENT DOCUMENTS

EP 1 477 226 A1 11/2004
EP 2 253 959 A1 11/2010
(Continued)

OTHER PUBLICATIONS

Search Report for PCT/IB2013/001009, dated Sep. 20, 2013.
Written Opinion for PCT/IB2013/001009, dated Sep. 20, 2013.

*Primary Examiner* — Jill A Warden
*Assistant Examiner* — Dwayne K Handy
(74) *Attorney, Agent, or Firm* — Marshall, Gerstein & Borun LLP

(57) ABSTRACT

A test tube, suitable to be immersed in a cryogenic fluid, comprises a containing body having a perimeter wall that defines a containing compartment, a bottom wall, disposed inside the latter to close it at the lower part, and a housing seating, inside the perimeter wall and outside the containing compartment. A support element for an identification code is suitable to be inserted into the housing seating, with at least a free surface facing toward the outside of the housing seating on the opposite side with respect to the bottom wall. In correspondence to said housing seating, mechanical constraint means are provided in cooperation with said perimeter wall of the containing body and with a peripheral portion of the free surface of the support element, in order to constrain the latter in a defined axial position with respect to the containing body.

17 Claims, 6 Drawing Sheets

(51) Int. Cl.
 *C12M 1/00* (2006.01)
 *G01N 1/42* (2006.01)
(52) U.S. Cl.
 CPC . *B01L 2300/022* (2013.01); *B01L 2300/0832* (2013.01); *B01L 2300/0851* (2013.01); *B01L 2300/0858* (2013.01); *B01L 2300/1894* (2013.01); *G01N 1/42* (2013.01); *Y10T 29/49826* (2015.01)
(58) Field of Classification Search
 CPC .......... B01L 2300/02; B01L 2300/021; B01L 2300/022; B01L 2300/023
 See application file for complete search history.

(56) References Cited

U.S. PATENT DOCUMENTS

| | | |
|---|---|---|
| 7,070,053 B1 | 7/2006 | Abrams et al. |
| 2009/0242446 A1* | 10/2009 | Abbott ................ B65D 25/205 206/459.5 |
| 2010/0007501 A1 | 1/2010 | Yang et al. |
| 2011/0199187 A1* | 8/2011 | Davidowitz ............ B01L 3/545 340/10.1 |
| 2012/0048827 A1* | 3/2012 | Levin .................... B01L 3/5082 215/329 |

FOREIGN PATENT DOCUMENTS

| | | |
|---|---|---|
| FR | 2 923 164 A1 | 5/2009 |
| FR | 2 930 238 A1 | 10/2009 |

* cited by examiner

TEST TUBE WITH IDENTIFICATION DEVICE AND CORRESPONDING PRODUCTION METHOD

FIELD OF THE INVENTION

The present invention concerns a test tube provided with an identification device and usable for in vitro analyses, research, storage and sampling. The present invention also concerns the connected production method.

The test tubes can also be used in cryogenic systems and/or in biobanks and can have a plurality of shapes both as test tubes and with regard to stoppering or sealing systems.

The invention particularly concerns test tubes that have an identification device on their lower part, that is, on the bottom, consisting of an identification code associated to a support element.

BACKGROUND OF THE INVENTION

It is known that structures which use test tubes for the purposes described above use a chromatic code to distinguish different types of content, or different uses or treatment of the test tubes.

Test tubes are known that for this purpose have closing means, with predefined colors, which facilitate cataloging and recognition.

Test tubes are also known, in particular those intended for cryogenic treatments in nitrogen, to which an identification code is associated, either obtained directly or on a disc, which acts as a support element for the code, applied on the bottom of the test tubes. The code allows to identify, both easily and accurately, by means of automatic systems, the content or the specific use for that test tube, which is essential to avoid errors which can even have serious consequences.

In the case where the disc is applied, that is, to make the bottom so that it can carry the code, there are different systems which comprise co-extrusion or application or gluing.

In the case of application, a considerable precision is required in construction and it is also necessary to achieve a considerable applicative precision. Indeed the gluing or application under pressure must be such as to make the surfaces of the disc where the identification code is applied and those of the test tube which are in reciprocal contact adhere perfectly. This is necessary so as to prevent the liquid nitrogen being introduced between the disc and the test tube when the test tube is introduced into the cryogenic vat. If this happens, it is possible that, once the test tube is extracted, the nitrogen may explode, even eliminating the disc, depriving the test tube of its own identification device.

Indeed, the thrust exerted axially on the disc is considerable, because of the violent reaction that involves the nitrogen in its passage from liquid to gas, in contact with the air, which passage is characterized by a volumetric expansion factor equal to about 1:700.

Because of the nature of the processes needed to make said coupling precision, as well as the solidity of the coupling, said test tubes are costly.

One purpose of the present invention is therefore to make a test tube that allows to speed up the production process and the application on the test tube of the support element where the identification code is applied, thus reducing costs and production times.

Another purpose of the present invention is to make a test tube which can be identified and catalogued easily and quickly using a support element, on which the identification code is applied, which is reliable and resistant to passages from the low temperatures typical of cryogenics to environmental temperature.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

In accordance with the above purposes, a test tube according to the present invention, suitable to be immersed in a cryogenic fluid, comprises a containing body having a perimeter wall that defines a containing compartment. It also comprises a bottom wall, disposed inside the containing compartment to close it at the lower part, and a housing seating. The housing seating is inside the perimeter wall and outside the containing compartment, and is suitable to house a support element, such as for example a disc made of plastic material. The latter acts as a support for an identification code, with which it defines an identification device for the test tube, and has at least a free surface facing toward the outside of the housing seating, on the opposite side with respect to the bottom wall. According to a main characteristic of the present invention, in correspondence with the housing seating for the support element, mechanical constraint means are provided in cooperation with the perimeter wall of the containing body and with at least a peripheral portion of the free surface of the support element, in order to constrain the latter in a defined axial position with respect to the containing body.

The present invention therefore allows a correct, safe, stable and reliable positioning of the support element, guaranteed by the mechanical constraint means. Moreover, no particular production strategies are needed in terms of precision or working tolerances. In this way it is possible, advantageously, to use less precise workings of the containing body and the support element, which are quicker and more economical to make, with undoubted benefits in terms of convenience and productivity, while maintaining practicality and efficiency.

A further advantage of the present invention lies in the reduction of time needed to insert and apply the support element to the test tube to be identified. To be effective, this application does not need perfect adhesion of the surfaces of the support element and its housing seating, to such an extent that the procedures of gluing or application by interference can be completely avoided.

In possible variant embodiments, an RIFD tag can be provided in which the identification code is memorized. In some implementations the RIFD tag can be associated to the support element.

According to one characteristic of the present invention, in correspondence to the housing seating the perimeter wall of the containing body can be continuous in a circumferential direction, or discontinuous. If discontinuous, it defines one or more through apertures, which put the inside of the housing seating in communication laterally with the outside.

In some forms of embodiment of the present invention, the mechanical constraint means comprise at least an overhang, made by upsetting the lateral wall of the containing body, which can be carried out for example by heat or ultrasound, in the internal part of the perimeter wall with respect to the housing seating of the support element for the identification code.

In different variants of the test tube in question, the overhang can affect the entire perimeter of the perimeter wall, or only portions of it.

The overhang, coming into contact with the peripheral portion of the free surface of the support element when the latter is inside its own housing seating, keeps it in position, preventing the axial movement which would cause it to exit from the housing seating.

Further variant embodiments of the invention provide that the constraint means comprise at least a holding lip, obtained by bending the end edge of the perimeter wall toward the inside of the housing seating for the support element.

It also comes within the spirit of the invention to provide only one holding lip which affects the entire perimeter of the perimeter wall, or a plurality of lips which affect only part of the perimeter of the perimeter wall, in a discontinuous way.

It also comes within the spirit of the invention to provide that a test tube comprises combinations of the forms of embodiment described above, that is, that the mechanical constraint means are defined by overhangs and holding lips, combined according to specific needs of use.

In some forms of embodiment of the present invention, the support element is positioned in direct abutment, that is, in contact, against the bottom wall of the containing body.

According to some forms of embodiment of the present invention, means to discharge the cryogenic fluid are provided, interposed, for example, between the bottom wall and the support element and cooperating with the housing seating in order to put the latter into communication with the outside of the test tube, and to expel the cryogenic fluid from the housing seating.

In this way, when the test tube is extracted from the container in which it is immersed in the cryogenic fluid, the cryogenic fluid possibly present between the support element and the walls of the housing seating is discharged toward the outside of the housing seating. The expansion reaction of the cryogenic fluid is therefore prevented from causing the support element of the identification code to come out of its housing seating.

The discharge means, in one form of embodiment of the invention, comprise at least an intermediate cavity, inside the housing seating and communicating with one or more through apertures made in the perimeter wall of the containing body.

In some forms of embodiment of the invention, the discharge means comprise at least a first discharge channel, open toward the housing seating, made in the bottom wall and communicating with a corresponding through aperture made in the perimeter wall of the containing body.

A variant of the present invention provides that a plurality of first discharge channels diverge from a central chamber, which is also open toward the housing seating for the support element, toward corresponding through apertures made in the perimeter wall.

Other forms of embodiment provide that second discharge channels are made at least in a peripheral wall of the support element and which are at least partly open toward the housing seating and in communication with the outside of the containing body.

It comes within the spirit of a variant to provide that the second discharge channels are open toward the peripheral wall of the support element facing toward the bottom wall and which pass through the support element in a through manner.

Another variant provides that the second discharge channels are made on the peripheral wall of the support element facing toward the bottom wall and which are positioned in communication with corresponding through apertures made in the perimeter wall of the containing body.

In another variant of the invention, the second discharge channels are made both on the peripheral wall of the support element facing toward the bottom wall, and also on the lateral peripheral wall of the support element.

The present invention also concerns a method to make a test tube suitable to be immersed in a cryogenic fluid, comprising a first step in which a containing body is made with a perimeter wall which defines a containing compartment, a bottom wall, disposed inside the containing compartment to close it at the lower part, and a housing seating, inside the perimeter wall and outside the containing compartment, a second step in which a support element is made for an identification code, a third step, after the first step and the second step, in which the support element is inserted in the housing seating so that at least a peripheral portion of a free surface of the support element is facing toward the outside of the housing seating on the opposite side with respect to the bottom wall.

In possible forms of embodiment, the method provides to make discharge means to discharge the cryogenic fluid between the bottom wall and the support element which cooperate with the housing seating in order to connect the latter with the outside of the test tube and expel the cryogenic fluid from the housing seating.

Moreover, in some forms of embodiment the method comprises a fourth step, after the third step, in which, in correspondence to the housing seating for the support element, mechanical constraint means are made, located in cooperation with the perimeter wall of the containing body and with at least part of the peripheral portion of the free surface of the support element, in order to constrain the latter in a defined axial position with respect to the containing body. The support element is positioned in direct abutment against the bottom wall of the containing body.

BRIEF DESCRIPTION OF THE DRAWINGS

These and other characteristics of the present invention will become apparent from the following description of some forms of embodiment, given as a non-restrictive example with reference to the attached drawings wherein.

Figure 1:
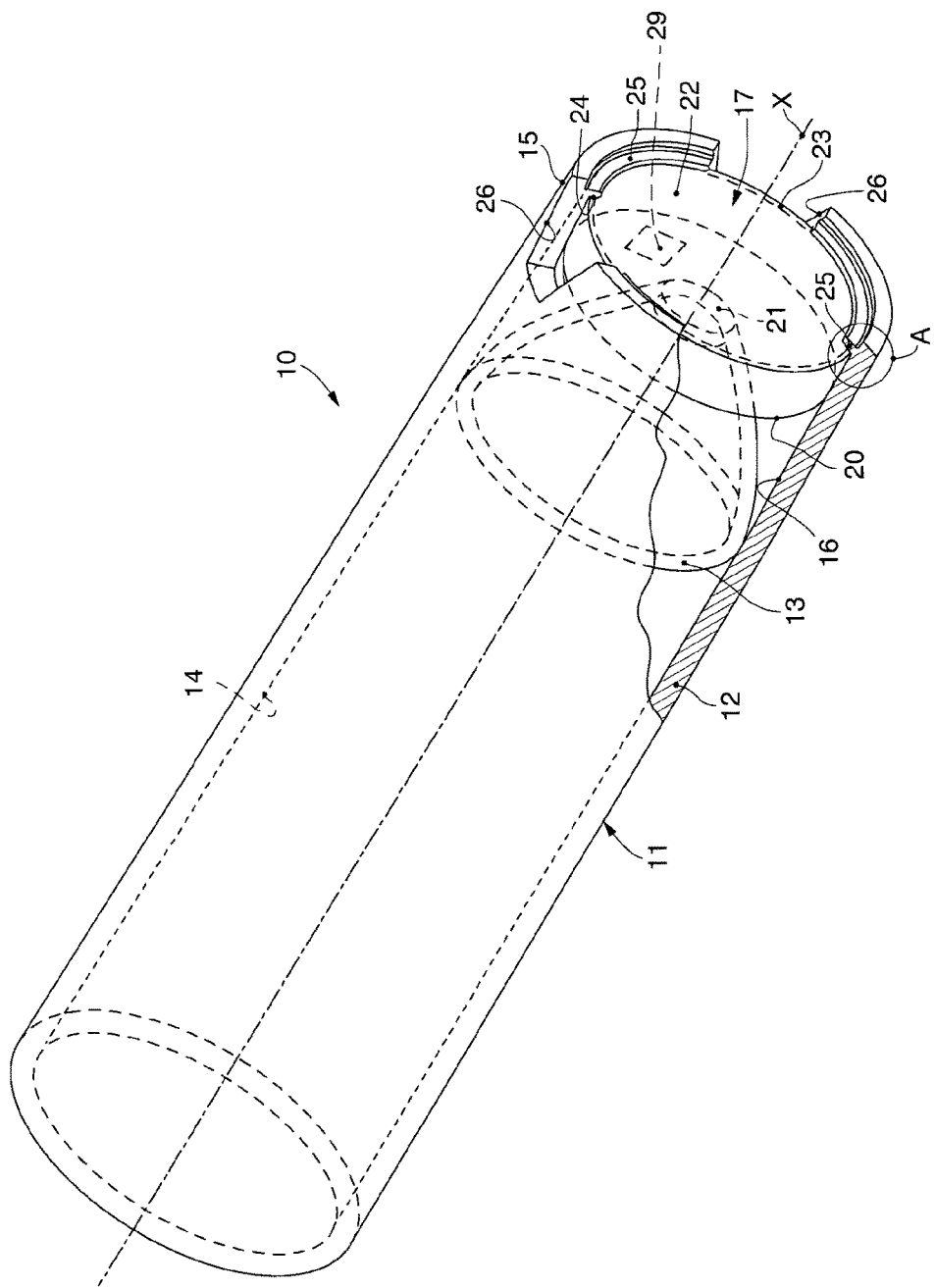
FIG. 1 is a three-dimensional view of a first form of embodiment of a test tube according to the present invention.

To facilitate comprehension, the same reference numbers have been used, where possible, to identify identical common elements in the drawings. It is understood that elements and characteristics of one form of embodiment can conveniently be incorporated in other forms of embodiment without further clarifications.

DETAILED DESCRIPTION OF SOME FORMS OF EMBODIMENT

With reference to the attached drawings, a test tube 10 made according to the present invention comprises a containing body 11 having in this case, merely by way of example, an elongated tubular shape along a longitudinal axis X, defined by a perimeter wall 12, which delimits a containing compartment 14 laterally. The bottom of the containing compartment 14 is defined by a bottom wall 13, transverse with respect to the longitudinal axis X and associated to the perimeter wall 12 at a determinate distance from one end 15 thereof.

The space inside the perimeter wall 12 and outside the bottom wall 13, comprised between the end 15 of the perimeter wall 12 and the bottom wall 13, defines a housing seating 16, in which a discoid element 17 is suitable to be inserted with play, which acts as a support element for an identification code of the test tube 10, not shown in the drawings.

In possible implementations, the identification code can be memorized in an RFID tag 29, shown as an example in FIG. 1; however it can be provided in all the forms of embodiment described using FIGS. 2-15. The RFID tag 29 can be the read-only type, or can be the writable or re-writable type. The identification code included in the RFID tag 29 can be read using a suitable RFID tag 29 reader.

The RFID tag 29 can be associated, for example applied stably, to the discoid element 17. One example of the position of the RFID tag 29 can for example be on the free surface 22. For example, it may be provided to glue the RFID tag 29. In another example the RFID tag 29 can be incorporated in the discoid element 17. Typically, the RFID tag 29 is positioned so that radio visibility is possible, for example so that it can be read for accessing and the information contained therein can be traced.

Figure 6:
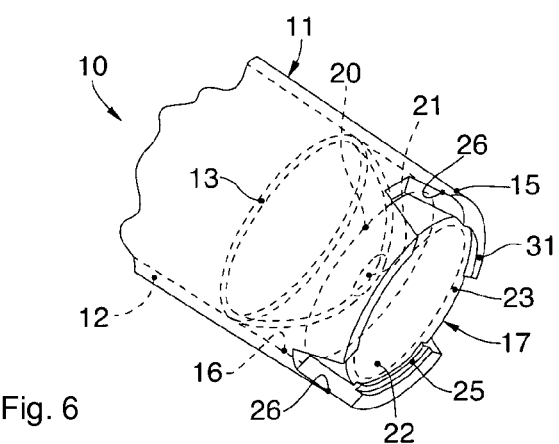
Figure 7:
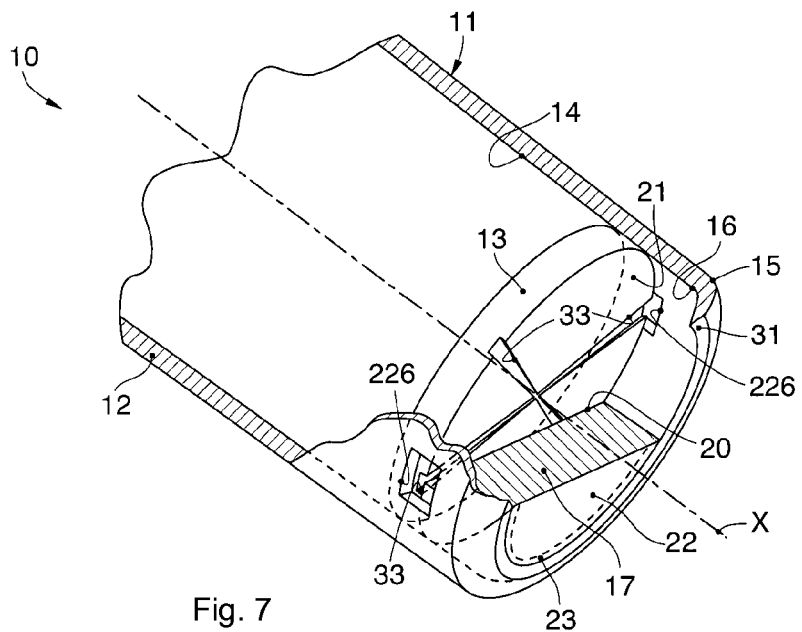
Figure 8:
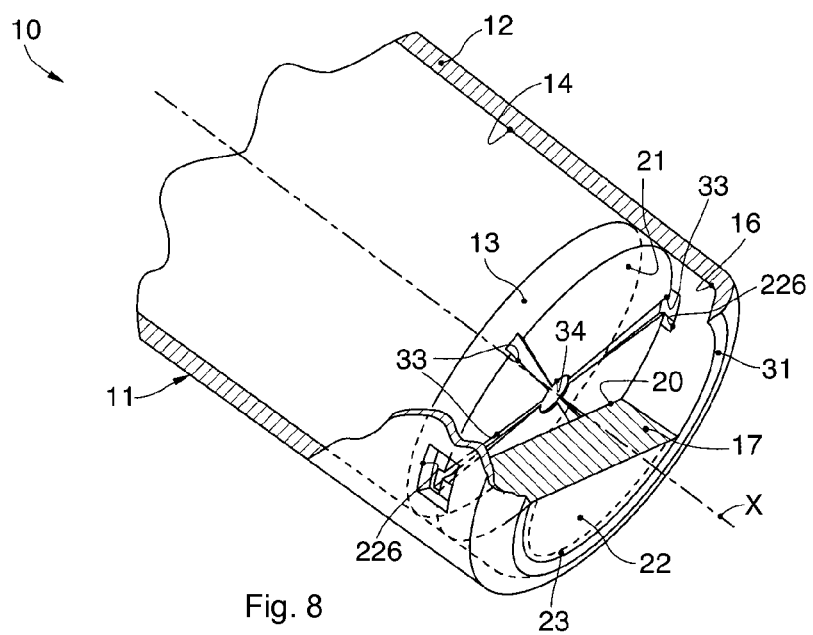
Figure 13:
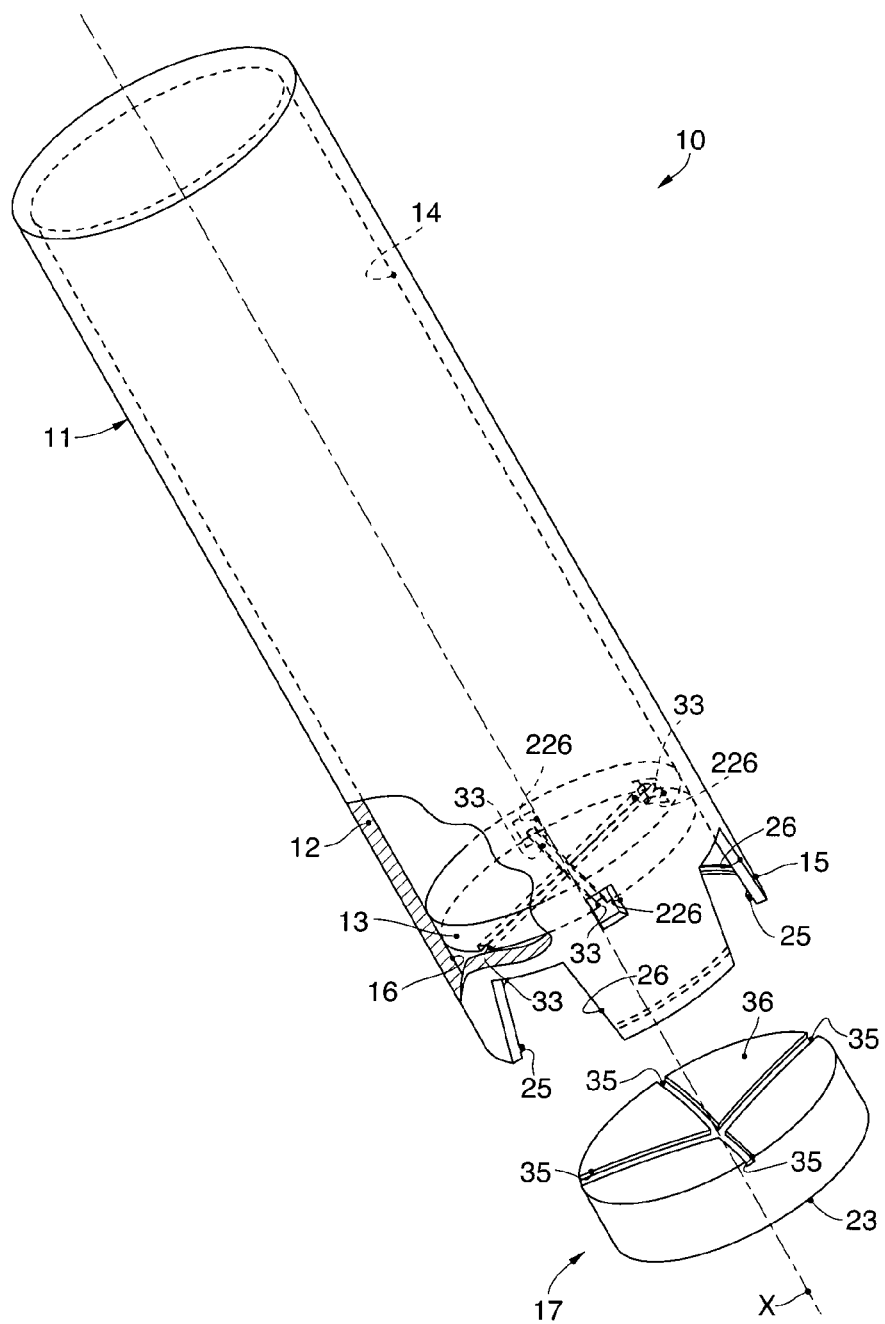
FIG. 13 is an exploded three-dimensional view of another form of embodiment of the test tube in FIG. 1.
Figure 14:
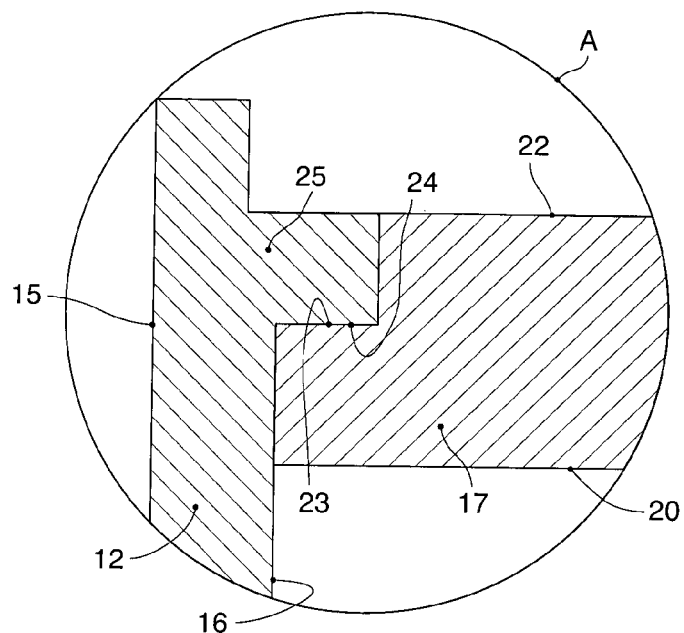
FIG. 14 is a section view of one form of embodiment of detail A in FIG. 1.
Figure 15:
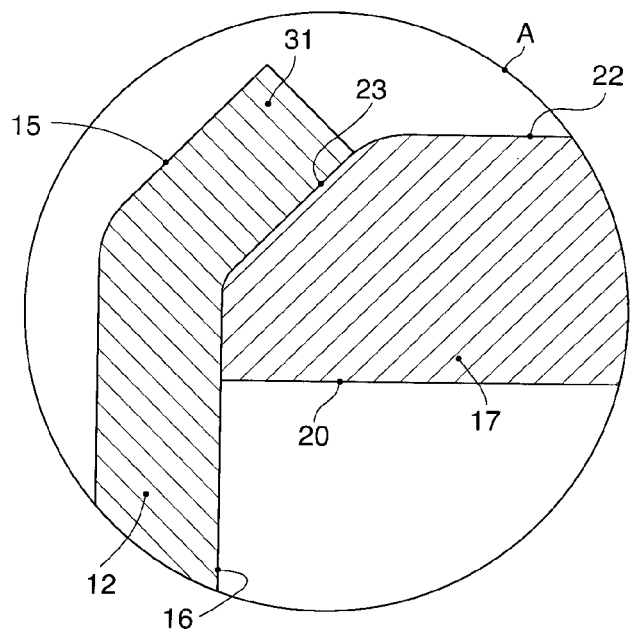
FIG. 15 is a variant of FIG. 14.

The bottom walls 13 can have different shapes, depending on the different production needs, and, for example, can be convex (FIGS. 1-6) and truncated cone shaped, or flat or discoid shaped (FIGS. 7, 8, 13).

In some forms of embodiment, the discoid element 17 and the bottom wall 13 are positioned in close proximity, once installed. In particular, in some forms of embodiment, the discoid element 17 is in direct abutment, that is, in contact, against the bottom wall 13 of the containing body 11.

During use, for example, when the discoid element 17 is positioned inside the housing seating 16, a first peripheral surface 20 thereof, and an external surface 21 of the bottom wall 13 are in contact with each other. This coupling allows the discoid element 17 to remain substantially orthogonal to the longitudinal axis X.

A free surface 22 of the discoid element 17, opposite the first peripheral surface 20, and therefore facing toward the outside of the housing seating 16, has a peripheral portion 23, which can affect only part, or the whole extension of the free surface 22, which rests on a supporting surface 24 of an overhang 25, made in proximity to the end 15 of the perimeter wall 12 and facing toward the longitudinal axis X.

In one form of embodiment (FIG. 14), it may be provided that in the part of the discoid element 17 facing toward the outside of the housing seating 16 a shoulder is made that defines the peripheral portion 23, disposed parallel to the free surface 22.

In a variant (FIG. 15), at least the part of the discoid element 17 facing toward the outside of the housing seating 16 is truncated cone shaped, so as to define the peripheral portion 23, which is inclined with respect to the free surface 22.

The overhang 25, obtained by the plastic deformation of the perimeter wall 12, and which advantageously can be obtained by hot or ultrasound upsetting, has the function of mechanically constraining the discoid element 17 inside the housing seating 16, preventing it from translating along the longitudinal axis X.

The mechanical constraint is effective both against gravity and against the thrust exerted by the expansion of the cryogenic fluid. In fact, gravity could cause the discoid element 17 to come out of the housing seating 16 if the end 15 were positioned below the perimeter wall 12. Furthermore, the cryogenic fluid, which can be for example nitrogen, if present in the housing seating 16, when it passes from the liquid state to the gaseous state, expands violently and can expel the discoid element 17.

In this case, the end 15 of the perimeter wall 12 of the containing body 11 is discontinuous in a circumferential direction and is shaped so as to define three through apertures 26, which put the housing seating 16 into communication with the outside of the test tube 10. In this way, the through apertures 26 function as a mean to discharge the nitrogen, allowing the latter to come out of the housing seating 16.

Figure 2:
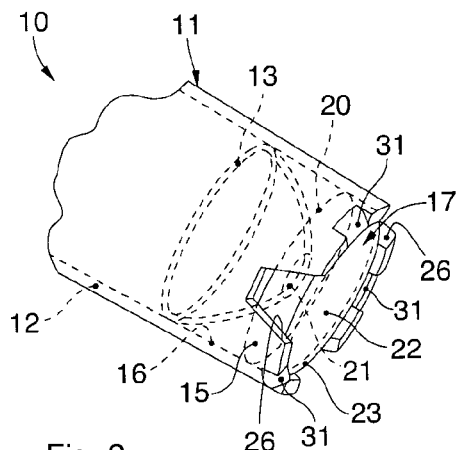
FIG. 2 is a three-dimensional view of detail A in FIG. 1.
Figure 3:
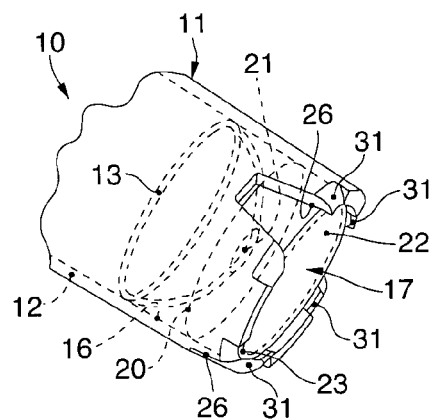
FIGS. 3-8 show further forms of embodiment of the detail A in FIG. 2.
Figure 4:
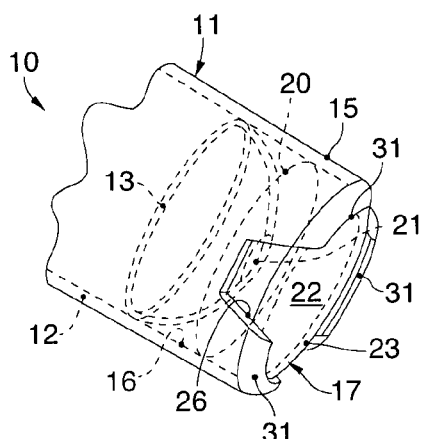
Figure 5:
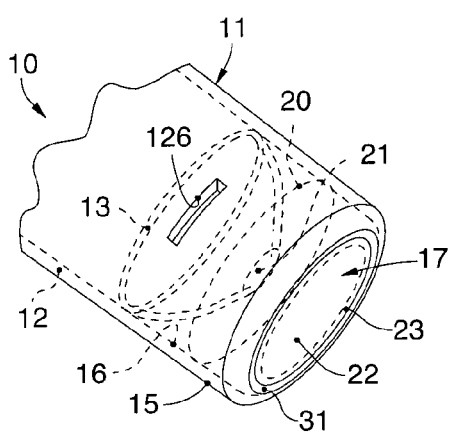

FIG. 2 shows a second form of embodiment of the test tube 10 and differs from the previous one in the mechanical constraint means of the discoid element 17 which, in this form of embodiment, consist of lips 31 bent back over the peripheral portion 23 of the free surface 22 of the discoid element 17. The lips are obtained, in this case, by hot or ultrasound bending of the central part of the portion of perimeter wall 12 which, in correspondence with the end 15, is comprised between two through apertures 26.

Variants of this form of embodiment (FIGS. 3 and 4) provide that the whole perimeter is bent, or only the lateral parts, of the portion of perimeter wall 12 comprised between two through apertures 26.

In another variant (FIG. 5), the perimeter wall 12, at its end 15, has a continuous circumferential development and is completely bent toward the peripheral portion 23 of the free surface 22 of the discoid element 17, to define a single lip 31. In this variant the through apertures 26 are replaced by slits 126, which have the same function of allowing to discharge the gas from inside the housing seating 16 toward the outside.

One form of embodiment of the test tube 10, shown in FIG. 6 and the result of the combination of forms of embodiment described above, comprises both overhangs 25 and a lip 31.

In another form of embodiment of the test tube 10 (FIG. 7) means 33, 35 to discharge the cryogenic fluid may be provided, between the bottom wall 13 and the discoid element 17, which are configured to cooperate with the housing seating 16 in order to connect the latter with the outside of the test tube 10 and to expel the cryogenic fluid from the housing seating 16. In possible implementations, for example, in the bottom wall 13 first discharge channels 33 are made, which can function as discharge means, or first discharge means, which for example are open toward the housing seating 16 and communicate with each other in correspondence with the longitudinal axis X of the containing body 11. Furthermore, each first discharge channel 33 communicates with a corresponding through aperture 226 made in the peripheral wall 12 of the containing body 11, to expel the cryogenic fluid.

In a variant of the previous form of embodiment (FIG. 8), in correspondence with the longitudinal axis X, there is a central chamber 34, suitable to collect the cryogenic fluid and from which the first discharge channels 33 diverge from the center of the bottom wall 13 toward the outside, where they communicate with the through apertures 226 described above.

Figure 9:
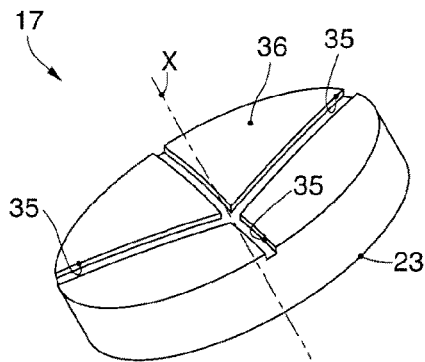
FIGS. 9-12 show different forms of embodiments of a component of FIG. 1.
Figure 10:
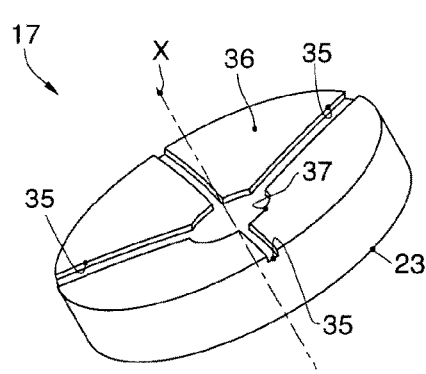

With reference to FIGS. 9 and 10, different forms of embodiment of the discoid element 17 comprise second discharge channels 35, made in its upper wall 36 and open toward the housing seating 16, which can function as discharge means. The second discharge channels 35, also called second discharge means, can communicate with each other and can be divergent from the longitudinal axis X toward the outside (FIG. 9), or all communicating with a central chamber 37, also made in the upper wall 36 of the discoid element 17, and can diverge from it radially toward the outside (FIG. 10).

During use, the second discharge channels 35 each communicate with a corresponding through aperture 26, 226, or with a slit 126.

The form of embodiment in FIG. 10 differs from the previous ones in that the second discharge channels 35 are made both in the upper wall 36 of the discoid element 17, and also in its lateral wall 38, to communicate directly toward the outside of the test tube 10.

Figure 11:
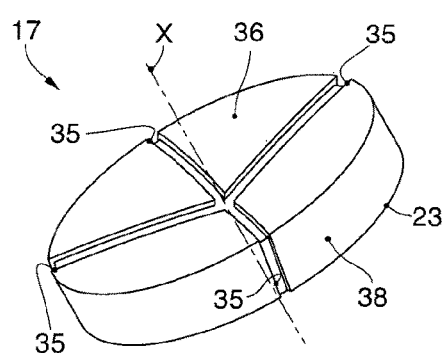
Figure 12:
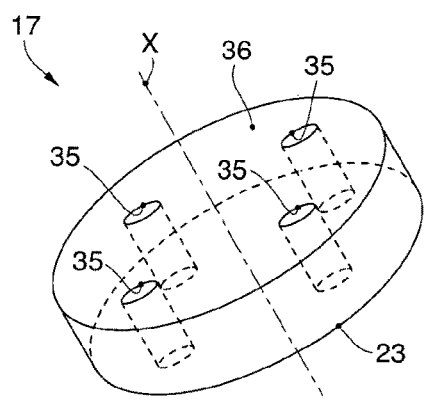

In FIG. 11, the second discharge channels 35 are made through in the discoid element 17, substantially parallel to the longitudinal axis X.

It is possible to provide any combination whatsoever of the forms of embodiment and variants described heretofore, as indicated by way of example in FIG. 13.

It is clear that modifications and/or additions of parts may be made to the test tube as described heretofore, without departing from the field and scope of the present invention.

It is also clear that, although the present invention has been described with reference to some specific examples, a person of skill in the art shall certainly be able to achieve many other equivalent forms of test tube, having the characteristics as set forth in the claims and hence all coming within the field of protection defined thereby.

The invention claimed is:

1. Test tube, suitable to be immersed in a cryogenic fluid, comprising a containing body having a perimeter wall that defines a containing compartment, the perimeter wall having a through aperture adjacent an end, a bottom wall having an opening, disposed inside said containing compartment to close it at the lower part, and a housing seating, inside said perimeter wall and outside said containing compartment, a support element sized for insertion in the housing seating, the support element including an identification code, said support element having at least a free surface facing toward the outside of said housing seating on the opposite side with respect to said bottom wall, and including an outlet channel formed by cooperating portions of the bottom wall and the support element and arranged to cooperate with the aperture of the perimeter wall and the opening of the bottom wall to discharge said cryogenic fluid outside of said test tube to thus expel said cryogenic fluid from said housing seating via the through aperture, and mechanical constraint means for constraining defined at least in part by a portion of said perimeter wall of said containing body and with a peripheral portion of said free surface of said support element, in order to constrain the support element in a defined axial position with respect to said containing body, said support element directly abutting against said bottom wall.

2. Test tube as in claim 1, wherein the identification code is stored in an RFID tag.

3. Test tube as in claim 2, wherein the RFID tag is disposed adjacent an outside portion of the support element.

4. Test tube as in claim 1, wherein said mechanical constraint means comprise at least one overhang, made in the internal part of said perimeter wall with respect to said housing seating.

5. Test tube as in claim 4, wherein said at least one overhang has at least one support surface able to cooperate with said peripheral portion of said free surface of said support element, to constrain it axially inside said housing seating.

6. Test tube as in claim 4, wherein said at least one overhang is obtained by upsetting one end of said perimeter wall.

7. Test tube as in claim 1, wherein said constraint means comprise at least a holding lip, made in the lower end edge of said perimeter wall, protruding toward the inside of said housing seating, and at least partly located in contact with said peripheral portion of said free surface of said support element, to constrain it axially inside said housing seating.

8. Test tube as in claim 7, wherein said at least one lip is made by bending at least part of one end of said perimeter wall.

9. Test tube as in claim 1, wherein, in correspondence to said housing seating, said perimeter wall is discontinuous to define the through aperture or to define a plurality of through apertures.

10. Test tube as in claim 9, including a plurality of outlet channels, the plurality of outlet channels made in said bottom wall a diverge from a central chamber also made in said bottom wall and with the plurality of outlet channels arranged to open toward said housing seating for said support element and communicating with corresponding ones of the through apertures.

11. Test tube as in claim 1, and further including additional outlet channels made in an upper wall of said support element, facing toward said bottom wall, said additional outlet channels being at least partly open toward said housing seating.

12. Test tube as in claim 1, and including additional outlet channels made in a lateral wall of said support element and facing toward said perimeter wall, said additional outlet channels being at least partly open toward said housing seating and toward the outside of said test tube.

13. Test tube as in claim 1, wherein said additional outlet channels are made through in said support element, to put said housing seating in communication with the outside of said test tube.

14. Method to make a test tube suitable to be immersed in a cryogenic fluid, comprising a first step in which a containing body is made, having a perimeter wall that defines a containing compartment, the perimeter wall having a through aperture adjacent an end, a bottom wall having an opening, disposed internally to said containing compartment to close it at the lower part, and a housing seating, inside said perimeter wall and outside said containing compartment, a second step in which a support element for an identification code is made, a third step, after said first and said second step, in which said support element is inserted into said housing seating, so that at least a peripheral portion of a free surface of said support element is facing toward the outside of said housing seating on the B opposite side with respect to said bottom wall, wherein said support element includes an outlet channel formed by cooperating portions of the bottom wall and the support element and arranged to cooperate with the aperture of the perimeter wall and the opening of the bottom wall to discharge said cryogenic fluid to outside of the of said test tube via the through aperture, and in that it also comprises a fourth step, after said third step, in which mechanical constraint means are made in correspondence to said housing seating for said support element, located in cooperation with said perimeter wall of said containing body and with at least part of said peripheral portion of said free surface of said support element, in order to constrain the latter in a defined axial position with respect to said containing body, said support element being positioned in direct abutment against said bottom wall.

15. Method as in claim 14, wherein during said fourth step a deformation of said perimeter wall is carried out, to obtain said mechanical constraint means.

16. Method as in claim 15, wherein said deformation carried out during said fourth step is made by bending at least a portion of an end of said perimeter wall.

17. Method as in claim 15, wherein said deformation carried out during said fourth step is obtained by upsetting at least a portion of an end of said perimeter wall.

\* \* \* \* \*